(12) United States Patent
Swaminathan et al.

(10) Patent No.: US 7,102,001 B2
(45) Date of Patent: Sep. 5, 2006

(54) PROCESS FOR PREPARING PYRROLOTRIAZINE

(75) Inventors: Shankar Swaminathan, Monmouth Junction, NJ (US); Ashvinikumar V. Gavai, Princeton Junction, NJ (US); Junying Fan, Monmouth Junction, NJ (US); Bharat P. Patel, Pennington, NJ (US); Derek J. Norris, Pennington, NJ (US); Richard Michael Corbett, Robbinsville, NJ (US); Bin Zheng, Kendall Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 11 days.

(21) Appl. No.: 11/008,719

(22) Filed: Dec. 9, 2004

(65) Prior Publication Data

US 2005/0209454 A1 Sep. 22, 2005

Related U.S. Application Data

(60) Provisional application No. 60/529,347, filed on Dec. 12, 2003.

(51) Int. Cl.
| | | |
|---|---|---|
| C07D 487/14 | (2006.01) | |
| C07D 413/14 | (2006.01) | |
| C07D 403/12 | (2006.01) | |
| A61K 31/53 | (2006.01) | |
| A61P 35/00 | (2006.01) | |

(52) U.S. Cl. .................... 544/183; 544/132; 548/362.1
(58) Field of Classification Search ................ 544/183, 544/132
See application file for complete search history.

(56) References Cited

U.S. PATENT DOCUMENTS

| 6,670,357 B1 | 12/2003 | Leftheris et al. |
| 6,787,545 B1 | 9/2004 | Ohtani et al. |
| 6,867,300 B1 | 3/2005 | Godfrey, Jr. et al. |
| 6,869,952 B1 | 3/2005 | Bhide et al. |
| 6,908,916 B1 | 6/2005 | Mastalerz et al. |
| 6,916,815 B1 | 7/2005 | Vite et al. |
| 2003/0232831 A1 | 12/2003 | Dyckman et al. |
| 2003/0232832 A1 | 12/2003 | Lombardo et al. |
| 2004/0063707 A1 | 4/2004 | Bhide et al. |
| 2004/0063708 A1 | 4/2004 | Bhide et al. |
| 2004/0077858 A1 | 4/2004 | Bhide et al. |
| 2004/0229877 A1 | 11/2004 | Leftheris et al. |

FOREIGN PATENT DOCUMENTS

| EP | 0 713 876 | 5/1996 |
| WO | WO 98/08847 | 3/1998 |
| WO | WO 00/71129 | 11/2000 |
| WO | WO 02/40486 | 5/2002 |
| WO | WO 03/090912 | 11/2003 |
| WO | WO 2004/009784 | 1/2004 |

OTHER PUBLICATIONS

Diphenyl phosphorazide, Encyclopoedia of Reagents for Organic Synthesis, edited by Pacquette, pp. 1-7 2003.*
Phosphorus Oxychloride, Encyclopedia of Reagents for Organic Synthesis, edited by Pacquette, pp. 1-12, 2003.*
Dimethyl chloromethyleneammonium chloride, (Vilsmeier reagent), Encyclopedia of Reagents for Organic Synthesis, edited by Pacquette, pp. 1-8, 2003.*
U.S. Appl. No. 11/019,899, filed Dec. 22, 2004, Gavai et al.
U.S. Appl. No. 11/019,901, filed Dec. 22, 2004, Fink et al.
Ewald, H. et al., "Reaktionen von, 1,2,4-Triazinen mit Acetylendicarbonsäure-dimethylester", Liebigs Ann. Chem., pp. 1718-1724 (1977).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-f]-1,2,4-triazine Derivatives", J. Heterocyclic Chem., vol. 16, pp. 833-834 (1979).
Neunhoeffer, H. et al., "Cycloadditionen mit Methoxy- und Dialkylamino-1,2,4-triazinen", Liebigs Ann. Chem., pp. 1413-1420 (1977).
Patil, S.A. et al., "Synthesis of Pyrrolo[2,1-f][1,2,4]triazine Congeners of Nucleic Acid Purines via the N-Amination of 2-Substituted Pyrroles", J. Heterocyclic Chem., vol. 31, pp. 781-786 (1994).
Quintela, J.M. et al., "A Ready One-pot Preparation for Pyrrolo[2,1-f][1,2,4]triazine and Pyrazolo[5,1-c]pyrimido[4,5-e]-[1,2,4]triazine Derivatives", Tetrahedron, vol. 52, No. 8, pp. 3037-3048.
U.S. Appl. No. 60/620,784, filed Oct. 21, 2004, Gavai et al.
U.S. Appl. No. 11/152,650, filed Jun. 14, 2005, Cai et al.
U.S. Appl. No. 11/157,460, filed Jun. 21, 2005, Gavai et al.

* cited by examiner

*Primary Examiner*—Venkataraman Balasubramanian
(74) *Attorney, Agent, or Firm*—Elliott Korsen

(57) ABSTRACT

The present invention provides a process for preparing compounds of formula (I)

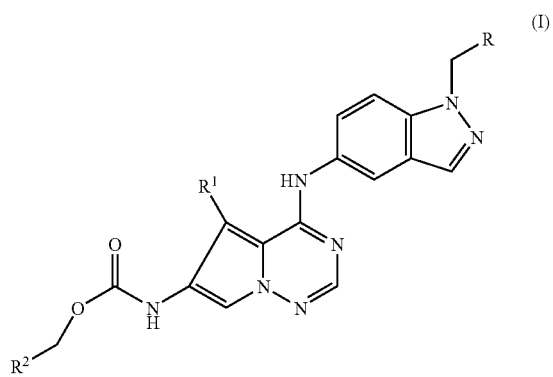

or a pharmaceutically acceptable salt thereof.

The compounds prepared by the process of the invention inhibit tyrosine kinase activity of growth factor receptors such as HER1, HER2 and HER4 thereby making them useful as antiproliferative agents for the treatment of cancer and other diseases.

6 Claims, No Drawings

PROCESS FOR PREPARING PYRROLOTRIAZINE

This application claims priority from U.S. Provisional Application No. 60/529,347 filed Dec. 12, 2003, the disclosure of which is incorporated herein by reference in its entirety.

FIELD OF THE INVENTION

This invention relates to a novel, improved processes for the preparation of pyrrolotriazine compounds that inhibit the tyrosine kinase activity of growth factor receptors such as HER1, HER2, and HER4 thereby making them useful as anti-cancer agents. The compounds prepared by the processes of the invention are also useful in the treatment of diseases, other than cancer, which are associated with signal transduction pathways operating through growth factor receptors such as HER1, HER2 and HER4.

SUMMARY OF THE INVENTION

The present invention provides an improved process for the preparation of pyrrolotriazine compounds (I) and intermediates (Compounds A and C) for the preparation thereof.

The process of the invention comprises, in one embodiment, the steps of first, chlorinating the pyrrolotriazine core, adding the substituted indazole portion of the compound through an alkylation reaction and then, via Curtius rearrangement, adding the heterocyclic "tail" which contains an N-protected piece. The N-protected piece is subsequently deprotected to provide the compounds of the invention.

In a second embodiment, the invention provides processes for preparing the key intermediates that are amenable to large scale preparations and provides derivatives of high quality and significantly higher yield than previous processes.

DETAILED DESCRIPTION OF THE INVENTION

The present invention provides a process for the preparation of compounds of the formula

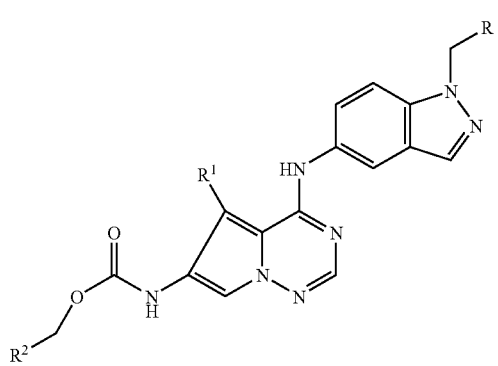

(I)

wherein
R is aryl, substituted aryl, heterocyclyl, or substituted heterocyclyl;
$R^1$ is alkyl or substituted alkyl;
$R^2$ is heterocyclyl or substituted heterocyclyl;

or a pharmaceutically acceptable salt or stereoisomer thereof, which comprises the steps of
reacting Compound II of the formula or a tautomer thereof

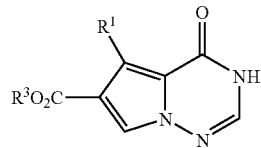

(II)

with an activating agent such as phosphorus oxyhalide or a Vilsmeier Reagent to afford Compound III of the formula, where
X is a leaving group such as Cl, Br, I or a phosphorus ester,
$R^1$ is as defined above, and
$R^3$ is lower alkyl

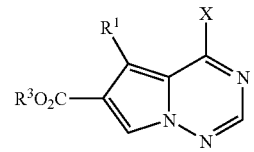

(III)

which is subsequently coupled with Compound IV of the formula

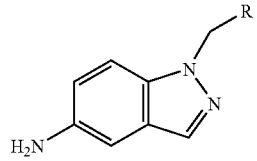

(IV)

where R is as defined above,
to afford Compound V of the formula

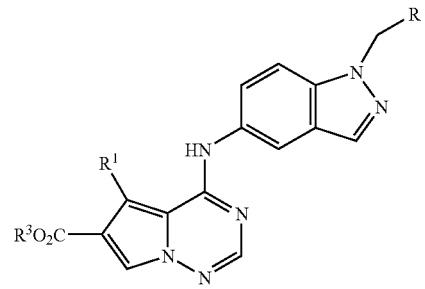

(V)

which is hydrolyzed to afford Compound VI of the formula

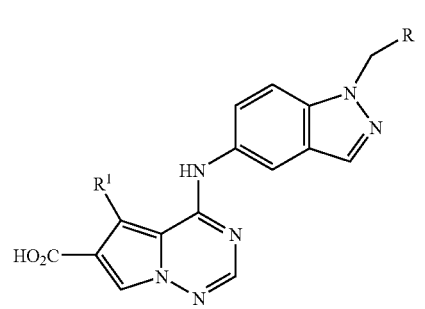

(VI)

which subsequently undergoes a Curtius rearrangement in the presence of a compound of the formula —R²CH₂OH to afford Compound I.

There is also disclosed a process for preparing the compound of the formula

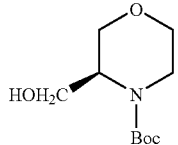

Compound A or a stereoisomer thereof, which comprises the steps of
reacting Compound VII of the formula

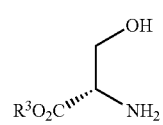

(VII)

or a salt thereof,
wherein R³ is alkyl, with a substituted or unsubstituted aryl aldehyde in the presence of a reducing agent to afford Compound VIII of the formula

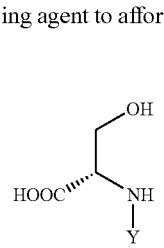

(VIII)

where Y is benzyl or a substituted benzyl group, which is subsequently reacted with an acylating agent in the presence of a mild alkaline buffer to afford Compound IX of the formula

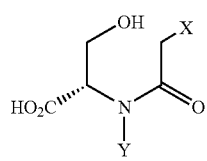

(IX)

where X is Cl, Br or I;
which is cyclized under strongly basic conditions to afford compound X of the formula

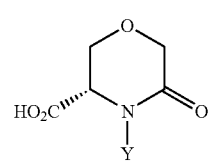

(X)

which is reduced to afford Compound XI of the formula

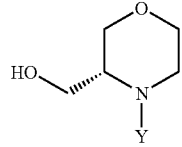

(XI)

which is debenzylated and then reacted with a suitable reagent to afford Compound A.

There is also disclosed a process for preparing a compound of the formula

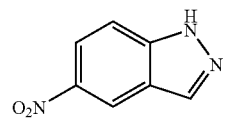

Compound C which comprises the steps of
a) alkylating a compound of the formula

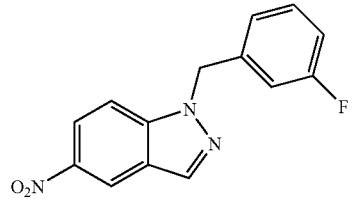

to afford a compound of the formula

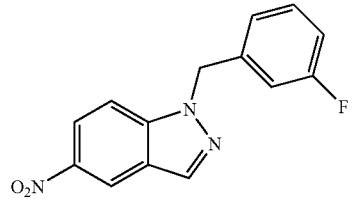

which is reduced to afford compound C.

In another embodiment, there is disclosed a process for preparing compound (Ia) of the formula

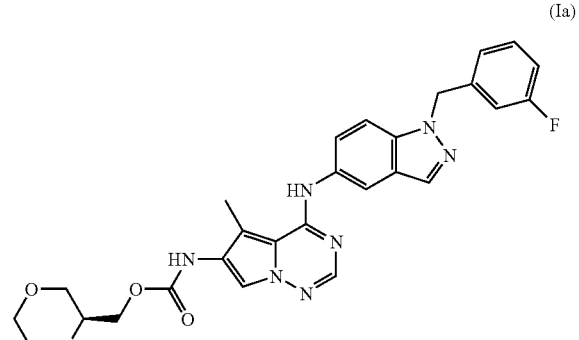

(Ia)

which comprises the steps of
reacting Compound B of the formula or a tautomer thereof

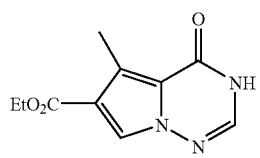

Compound B with an activating agent such as phosphorus oxyhalide, to afford Compound 18 of the formula

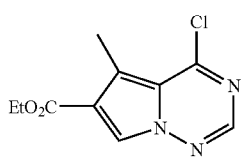

which is subsequently coupled to Compound C of the formula

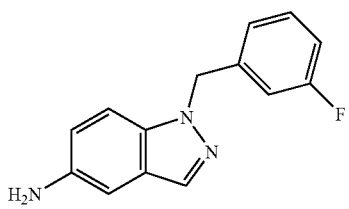

Compound C to afford Compound 19 of the formula

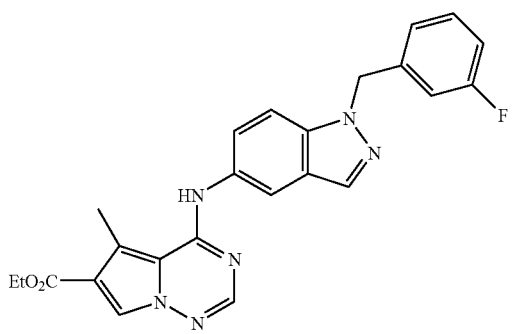

which is hydrolyzed to afford Compound 20 of the formula

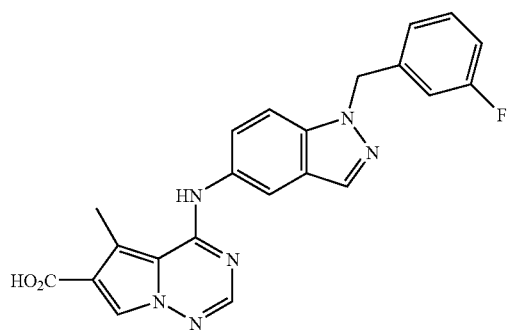

which subsequently undergoes a Curtius rearrangement in the presence of Compound A, to afford Compound 21 of the formula

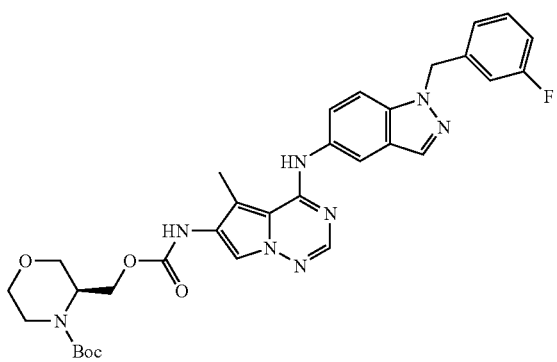

which is deprotected to afford Compound Ia.

The invention also provides a pharmaceutical composition comprising a compound of formula I and a pharmaceutically acceptable carrier, prepared by the process of the invention.

The invention also provides a pharmaceutical composition prepared by the process of the invention comprising a compound of formula I in combination with pharmaceutically acceptable carrier and an anti-cancer or cytotoxic agent. In one embodiment said anti-cancer or cytotoxic agent is selected from the group consisting of linomide; inhibitors of integrin αvβ3 function; angiostatin; razoxane; tamoxifen; toremifene; raloxifene; droloxifene; iodoxifene; megestrol acetate; anastrozole; letrozole; borazole; exemestane; flutamide; nilutamide; bicalutamide; cyproterone acetate; gosereline acetate; leuprolide; finasteride; metalloproteinase inhibitors; inhibitors of urokinase plasminogen activator receptor function; growth factor antibodies; growth factor receptor antibodies such as Avastin® (bevacizumab) and Erbitux® (cetuximab); tyrosine kinase inhibitors; serine/threonine kinase inhibitors; methotrexate; 5-fluorouracil; purine; adenosine analogues; cytosine arabinoside; doxorubicin; daunomycin; epirubicin; idarubicin; mitomycin-C; dactinomycin; mithramycin; cisplatin; carboplatin; nitrogen mustard; melphalan; chlorambucil; busulphan; cyclophosphamide; ifosfamide nitrosoureas; thiotepa; vincristine; Taxol® (paclitaxel); Taxotere® (docetaxel); epothilone analogs; discodermolide analogs; eleutherobin analogs; etoposide; teniposide; amsacrine; topotecan; irinotecan, flavopyridols; biological response modifiers and proteasome inhibitors such as Velcade® (bortezomib).

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclic groups, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole, indole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclic groups, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized or protected. Examples of this include N-protected morpholine.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzimidazolyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclic groups, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzmmology*, Vol. 42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

It should further be understood that solvates (e.g., hydrates) of the compounds of formula I are also within the scope of the present invention. Methods of solvation are generally known in the art.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisole or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.™. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent (s).

METHODS OF PREPARATION

Certain compounds of formula I may be prepared according to the following schemes and the knowledge of one skilled in the art.

All temperatures are in degrees Celsius (° C.) unless otherwise indicated. Preparative Reverse Phase (RP)HPLC purifications were done on C18 reverse phase (RP) columns YMC S5 ODS columns eluting with 90% aqueous methanol containing 0.1% TFA as buffer solution and monitoring at 220 nm. For analytical HPLC 0.2% phosphoric acid was used instead of TFA. All of the synthesized compounds were characterized by at least proton NMR and LC/MS. During work up of reactions, the organic extract was dried over magnesium sulfate ($MgSO_4$), unless mentioned otherwise.

The following abbreviations are used for the commonly used reagents. $Et_2O$; diethyl ether, $Na_2SO_4$; sodium sulfate; HCl; hydrochloric acid, NaOH; sodium hydroxide, NaCl; sodium chloride, Pd/C; palladium on carbon, $K_2HPO_4$; potassium monohydrogen phosphate, $K_2CO_3$; potassium carbonate, $NaHCO_3$; sodium bicarbonate, LiOH; lithium hydroxide, TMSCl, trimethylsilyl chloride, $H_2SO_4$, sulfuric acid, RT; room temperature, TFA; trifluoroacetic acid, h; hour.

The term "Vilsmeier Reagent" means either phosgene iminium chloride ($Cl_2C=N(CH_3)_2Cl$) or (chloromethylene) dimethylammonium chloride ($ClCH=N(CH_3)_2Cl$).

The term "activating agent" means phosphorus oxyhalide or Vilsmeier Reagent that converts the amide compound II to Compound III.

One aspect of the invention involves the preparation of two key intermediates, identified as Compounds A and C.

The original synthesis of Compound A was a very low yielding (overall yield ~8%) 4-step process. This synthesis is shown below:

Original Synthesis of Compound A

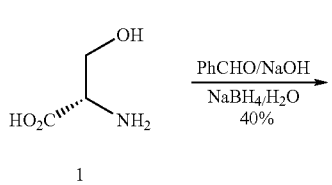

1 reducing agents used to convert Compound 5 to Compound 7 include catalytic hydrogenation agents and other substituted borohydrides. The yield of this step was increased from the original synthesis from 40% to 60–70%.

Step 2

Acylation/Cyclization

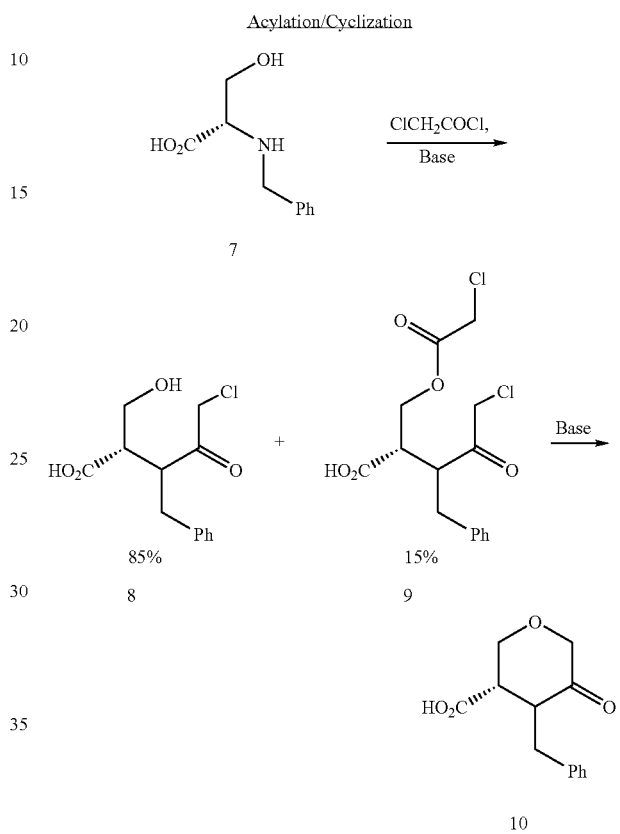

The acylation/cyclization step was improved by carrying out the acylation under Schotten-Baumann conditions using mild bases such as alkali metal carbonates, or alkali metal phosphates like disodium or dipotassium hydrogen phosphate. The cyclization of the acylated material was carried out at lower temperatures (<15° C. compared to the original protocol of 30° C.) and at pH>13. The yield of this step was increased from the original synthesis from 20–25% to 78–85%.

Step 3

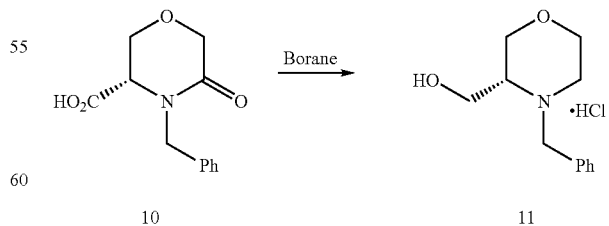

Various reagents were employed in the reduction including BH$_3$.Me$_2$S, LAH, Red-Al and lithium triethyl borohydride. Amongst the reagents tried, BH$_3$.Me$_2$S provided the best results and was utilized to improve the yield and quality

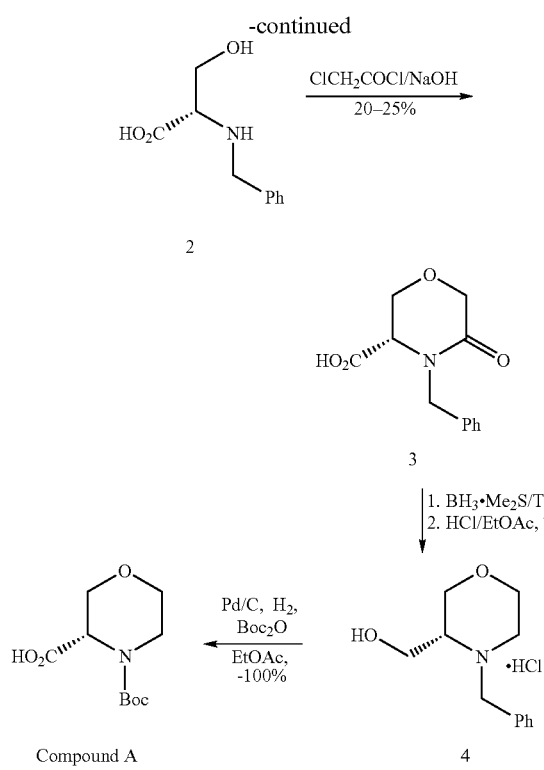

In the original synthesis, the N-benzylation and acylation/cyclization steps were low yielding. This synthesis was based on Brown et al., Journal of the Chemical Society, Perkin Transactions 1: Organic and Bio-Organic Chemistry 1985, 12, pgs 2577–80.

An improved synthesis of this compound was developed using the following steps:

Step 1

Benzylation

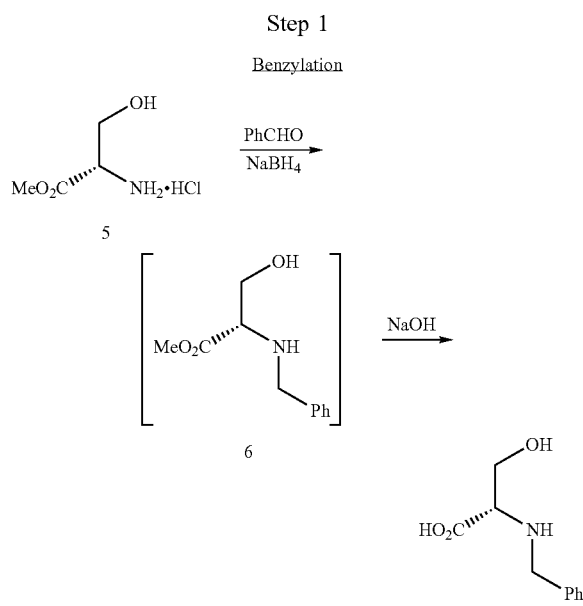

The benzylation step was improved by the use of L-serine methyl ester hydrochloride (5) as the starting material. Other of the desired product. Compound 10 was converted to an alkyl ester and subsequently reduced with LAH to afford compound 11.

Step 4

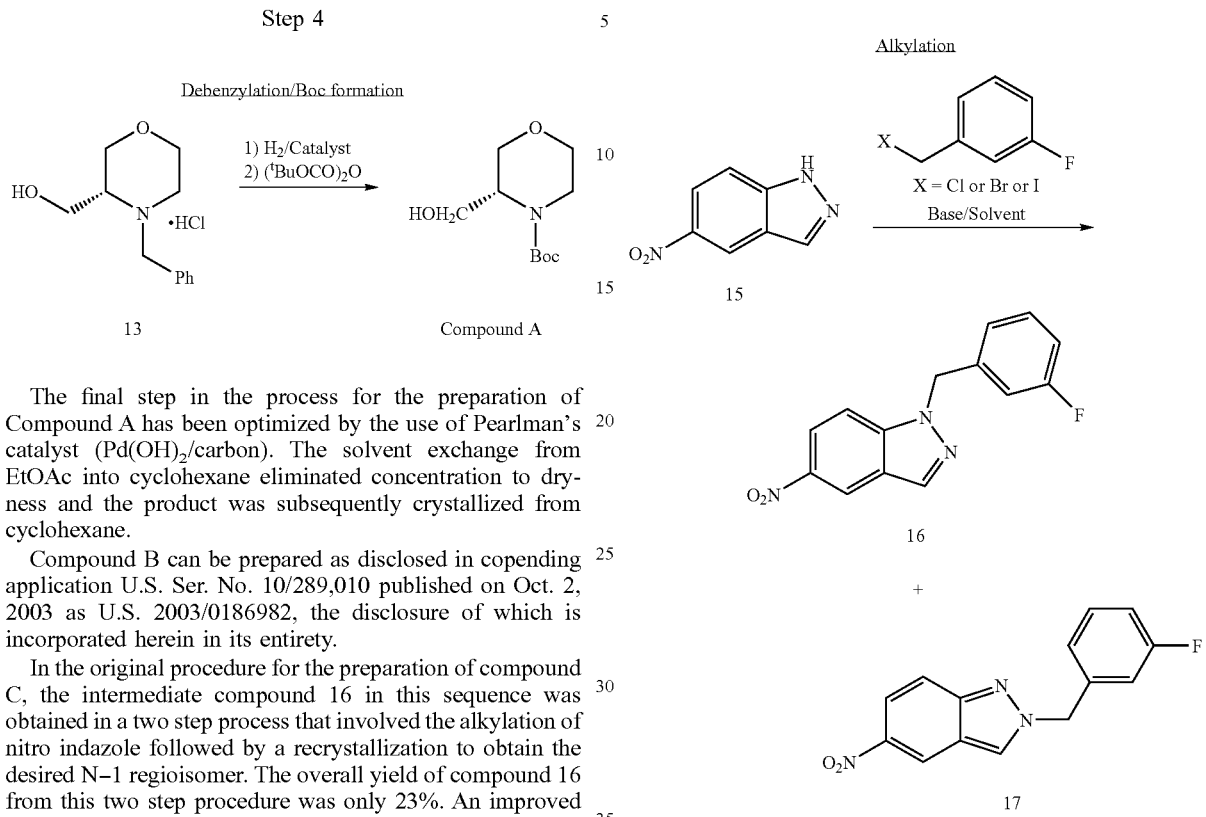

The final step in the process for the preparation of Compound A has been optimized by the use of Pearlman's catalyst (Pd(OH)$_2$/carbon). The solvent exchange from EtOAc into cyclohexane eliminated concentration to dryness and the product was subsequently crystallized from cyclohexane.

Compound B can be prepared as disclosed in copending application U.S. Ser. No. 10/289,010 published on Oct. 2, 2003 as U.S. 2003/186982, the disclosure of which is incorporated herein in its entirety.

In the original procedure for the preparation of compound C, the intermediate compound 16 in this sequence was obtained in a two step process that involved the alkylation of nitro indazole followed by a recrystallization to obtain the desired N-1 regioisomer. The overall yield of compound 16 from this two step procedure was only 23%. An improved process for compound C is shown below where the yield for the preparation of compound 16 rose to 49%.

The process is described in more detail below:

Step A

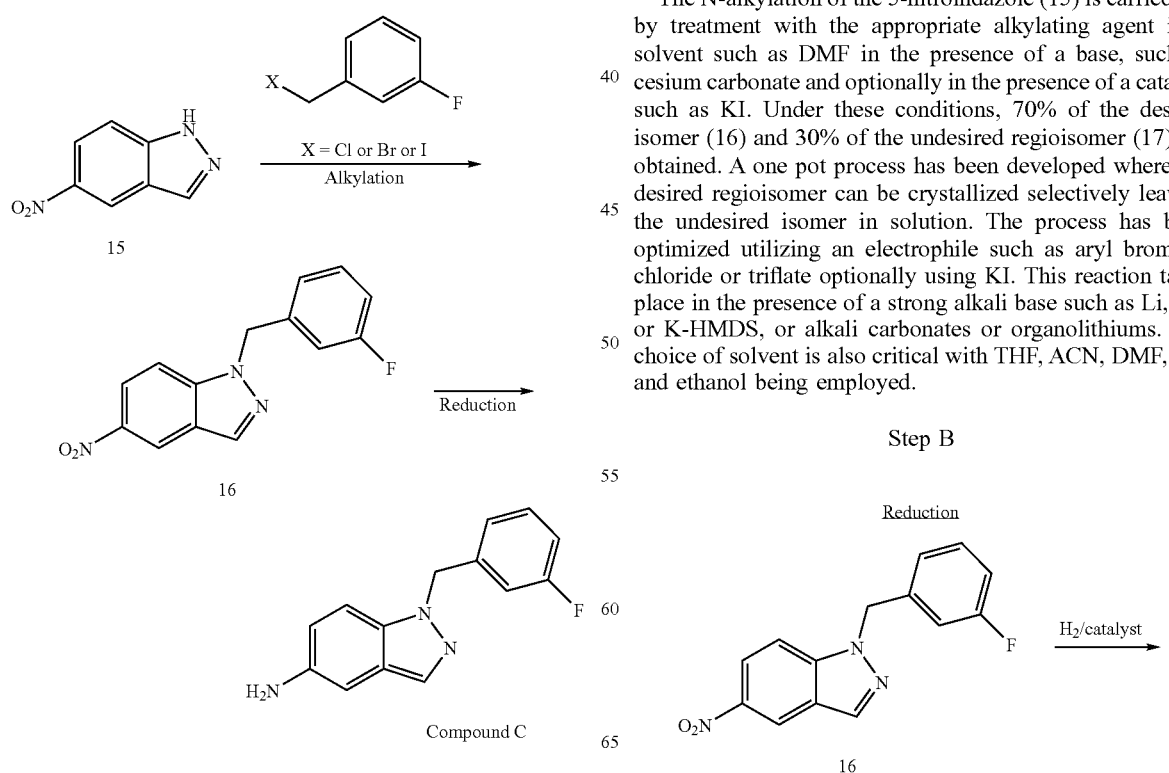

The N-alkylation of the 5-nitroindazole (15) is carried out by treatment with the appropriate alkylating agent in a solvent such as DMF in the presence of a base, such as cesium carbonate and optionally in the presence of a catalyst such as KI. Under these conditions, 70% of the desired isomer (16) and 30% of the undesired regioisomer (17) are obtained. A one pot process has been developed where the desired regioisomer can be crystallized selectively leaving the undesired isomer in solution. The process has been optimized utilizing an electrophile such as aryl bromide, chloride or triflate optionally using KI. This reaction takes place in the presence of a strong alkali base such as Li, Na, or K-HMDS, or alkali carbonates or organolithiums. The choice of solvent is also critical with THF, ACN, DMF, IPA and ethanol being employed.

Step B

Reduction

-continued

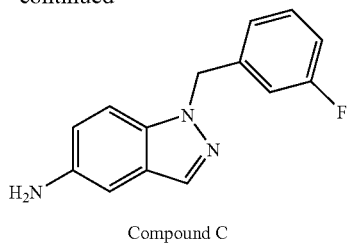

Compound C

The reduction step incorporates additional process improvements over prior syntheses. These include the use of THF instead of ethanol to prevent crystallization of the product during the reaction and carrying out the hydrogenation at lower pressure (5–15 psi) than in the original process (50 psi).

Step C

Chlorination/Alkylation

The final process for conversion of Compound B to Compound 19 via Compound 18 uses 1.8 eq phosphorus oxychloride and 1.2 eq diisopropylethylamine in 15 liters toluene per kilogram (Compound B) at reflux. The reaction was quenched with 6 eq aqueous potassium phosphate dibasic. The rich organic solution of Compound 18 is dried by azeotropic removal of water under reduced pressure to 4 liters per kilogram Compound B final concentration. Additions of Compound C (0.95 eq) and 1.2 eq diisopropylethylamine are followed by warming to 90° C. for 2–4 h. Upon completion, isopropyl alcohol is added to effect crystallization of Compound 19.

Other aqueous quench solutions include water, 1 N hydrogen chloride solution, potassium phosphate tribasic solution, and 1 N sodium hydroxide solution.

Other bases that may be used for the conversion of Compound B to Compound 18 include pyridine.

Use of N-methyl morpholine, DABCO, and pyridine in the conversion of Compound 18 to Compound 19 were evaluated and shown to lead to full or partial conversion.

Step D

The hydrolysis of the ethyl ester (compound 19) is carried out using alkali metal hydroxides. The preferred bases are aqueous sodium and potassium hydroxide. This takes place in a combination of hydroxylic and ether solvent at a temperature below 65° C. The carboxylic acid is precipitated from the reaction stream by addition of a mineral acid.

Step E

A mixture of compound 20, compound A, DDPA and an organic tertiary amine is heated at a temperature below 95° C. in an appropriate solvent. The intermediate acyl azide is generated in the presence of Compound A which resulted in minimizing formation of the urea impurity. The Curtius rearrangement can be carried out using polar or nonpolar aprotic solvents such as acetonitrile, toluene or xylene.

The complete synthesis of the compounds of the invention of formula (I) is shown below.

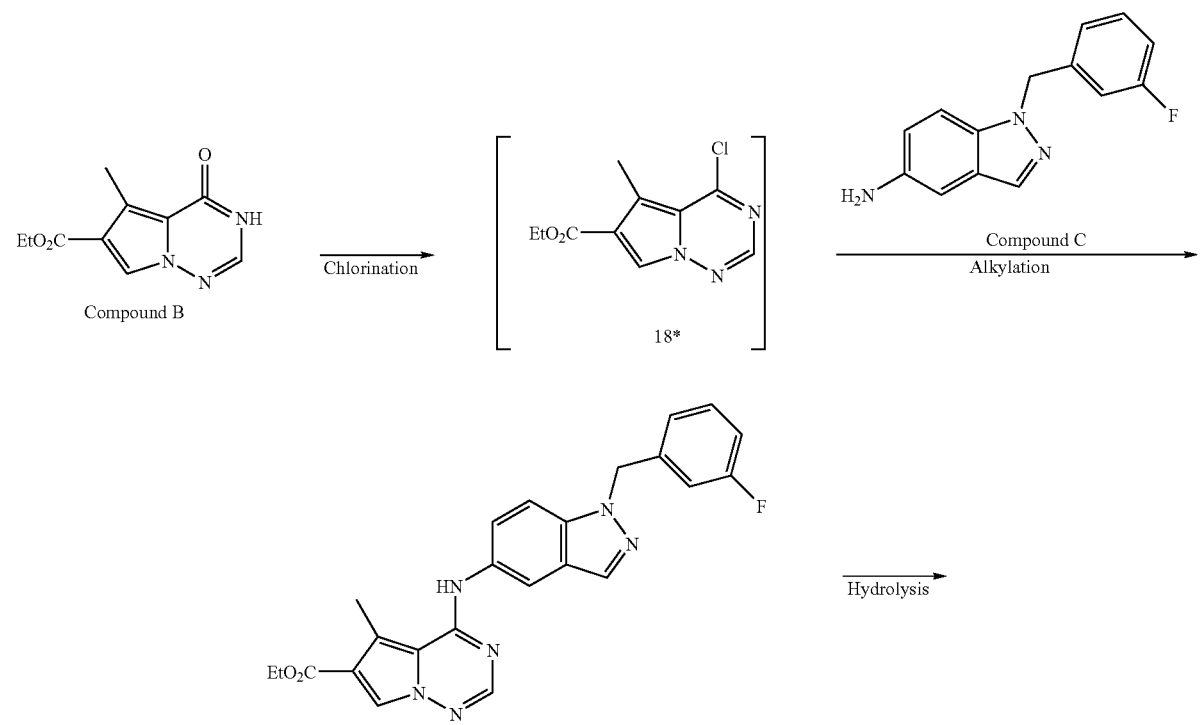

-continued
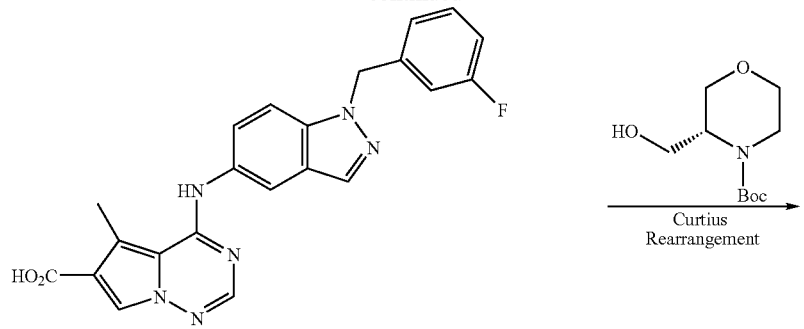
20
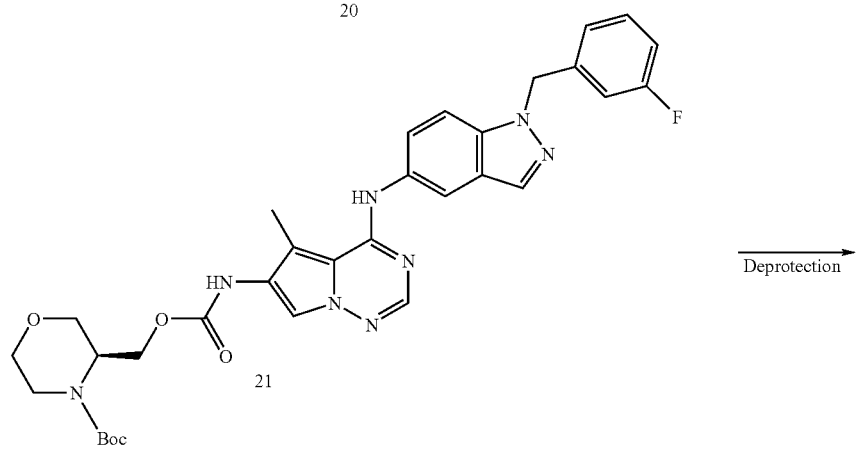
21
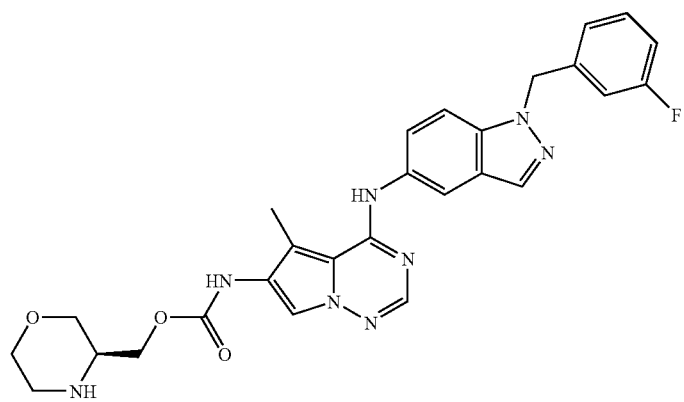
Compound Ia
Details of the above process are described below in Example 1.
EXAMPLE 1
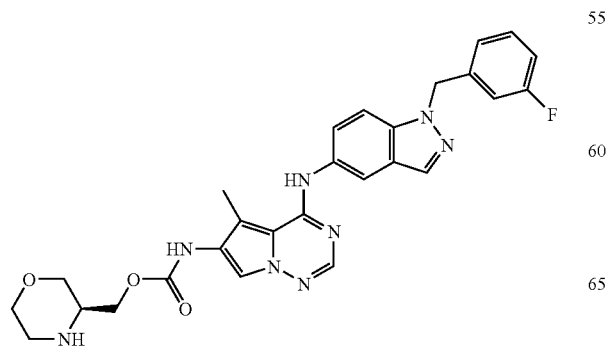

[4-[[1-(3-fluorophenyl)methyl]-1H-indazol-5-ylamino]-5-methyl-pyrrolo[2, 1-f ][1,2,4]triazin-6-yl]-carbamic acid, (3S)-3-morpholinylmethyl ester (Ia)

A. Preparation of 2-benzylamino-3-hydroxy-propionic acid and 2-dibenzylamino-3-hydroxy-propionic acid

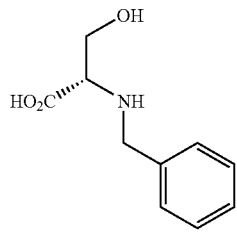

To a reaction vessel was added solid L-serine methyl ester hydrochloride (1.000 equiv.). Methanol (2.85 volumes) was added and agitation was started. Triethylamine (1 equiv.) was added over 10 min while maintaining the temperature from about 14° C. to about 18° C. Stirring was continued until all solids dissolved. The mixture was cooled to 10° C. and benzaldehyde (0.99 equiv.) was added over 15 min while maintaining the temperature between about 11° C. to about 15° C. The reaction was held for 30 min at about 8° C. to about 12° C. Solid sodium borohydride (4 equiv. of hydride) was added over 2 hr while maintaining the temperature at about 10° C. to about 20° C. The reaction was held for 30 min at about 14° C. to about 16° C. and then analyzed by HPLC.

In a separate flask, methanol (1.15 volumes) and water (1.72 volumes) were added. Sodium hydroxide, 50 wt/wt % in water (3.04 equiv.) was added, and the resulting solution was cooled to 15° C. The Schiff's base was transferred to this mixture over 1 hr maintaining the internal temperature between 16~22° C. The reaction was held for 30 min at 20° C. and analyzed by HPLC for consumption of methyl ester. Water (1.72 volumes) was added, followed by concentrated HCl, 12.2 M in water (2.67 equiv.) while maintaining the temperature at 15~25° C. to adjust the pH to 9.5. The mixture was filtered and the filter-cake was washed with two portions of water (0.58 volumes each). The washes were combined with the filtrate in a separatory funnel. The combined aqueous portions were washed two times with ethyl acetate (5.75 volumes each). The material was transferred from the separatory funnel to a flask. The mixture was cooled from 25° C. to 15° C., and concentrated HCl, 12.2 M in water (0.89 equiv.) was added until the pH of the mixture reached 6.5, while maintaining the temperature between 17–22° C. The mixture was held for 15~25 hr at 5° C., then the solids were collected on a filter funnel. The filter cake was washed with two portions of water (1.43 volumes each) and two portions of heptane (1.43 volumes each). The wet solid was transferred to a drying tray, and dried at 45° C. for 21 hr and the yield was 61%.

B. Preparation of 4-Benzyl-5-oxo-morpholine-3-carboxylic acid

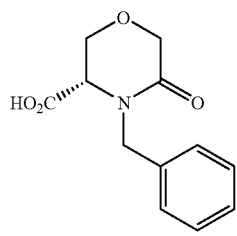

To a reactor was charged N-benzyl-L-serine (1.0 eq) and THF (6.1 volumes). The resulting solution was cooled to 0±5° C. and a pre-cooled solution (0–5° C.) of potassium carbonate (3.0 eq) in water (6.1 volumes) was added. Chloroacetyl chloride (1.4 eq) then was added via addition funnel while maintaining the internal temperature below 5° C. The biphasic reaction mixture was aged for approximately 30 min at 0±5° C. After aging, the mixture was sampled for HPLC analysis. If >6 area percent remaining N-benzyl-L-serine was present, additional chloroacetyl chloride was added. Once the reaction completeness specification has been met, 50 wt % sodium hydroxide is charged while keeping the internal temperature between 5 and 10° C. until the pH remains constant >13.5. The reaction was deemed complete when HPLC analysis showed <1 area percent (combined) intermediates. The mixture was warmed to 25° C., and heptane (2.03 volumes) was added. The mixture was stirred rapidly for 10 min, and then the phases were allowed to separate. The organic upper phase was discarded, and the rich aqueous phase was treated again with heptane (3.04 volumes). After stirring rapidly for 10 min, the phases were allowed to settle, and the organic upper phase was discarded. The rich aqueous portion was cooled to −5–0° C. and 37 wt % hydrochloric acid was added while maintaining a batch temperature <10° C. until pH <2. The resulting slurry was kept at −10–0° C. for a minimum of 4 h. The slurry was filtered over Whatman 1 filter paper, or equivalent, and washed with pre-cooled (3–7° C.) water (2×4.57 volumes). The wet cake was dried in vacuo at 40–45° C. After drying, 1.475 kg (84.9%, uncorrected) of 4-benzyl-5-oxo-morpholine-3-carboxylic acid was obtained. HPLC Ret Time: 1.82 min (YMC S5 ODS column 4.6×50 mm, 10–90% aqueous methanol over 4 minutes containing 0.2% phosphoric acid, 4 mL/min, monitoring at 220 nm); Chiral HPLC Ret Time: 7.94 min, e.e. 100%, (Chiralcel OJ-R, 150×4.6 mm, 5 μM, eluent: MeOH:0.2% aq. H$_3$PO4 [50:50], flow rate 1 mL/min, 210 nm).

C. Preparation of [R-(4-Benzyl-morpholin-3-yl)]-methanol hydrochloride

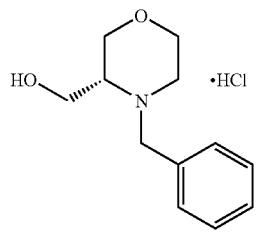

To a stirred mixture of 4-benzyl-5-oxo-morpholine-3-carboxylic acid (1 equiv.) in dry THF (16 volumes) under nitrogen was added triethyl amine (1.19 equiv.). To this mixture was added borane-methyl sulfide complex (7.45 equiv.) at such a rate that the temperature of the reaction mixture was kept below 10° C. The addition took 1 h. The reaction mixture was gently refluxed (65° C.) under nitrogen for 5.5 h. The mixture was cooled and MeOH (1.39 volumes) was added slowly (The internal temperature was kept below 25° C. during the addition and the addition took 1 h). To this resulting mixture was added water (4.18 volumes) and the mixture was stirred at room temperature overnight. The mixture was concentrated in vacuo and was diluted with 2N aqueous sodium hydroxide (4.59 equiv.) and water (1.74 volumes). This mixture was extracted with ethyl acetate (2×7 volumes). The combined ethyl acetate extracts were washed with a 20% aqueous sodium chloride solution (4.18 volumes). The ethyl acetate extracts were then concentrated in vacuo to give a crude oil. This oil was diluted with ethyl acetate (10.2 volumes) and methanol (0.52 volumes). To this solution was added trimethylsilyl chloride (352 mL, 0.61 volumes) dropwise until the pH of the solution was acidic. The batch temperature during the trimethylsilyl chloride addition temperature was kept below 20° C. At the end of the addition, the mixture was cooled at 0° C. for 2 h and the precipitate was collected by filtration to give [R-(4-Benzyl-morpholin-3-yl)]-methanol hydrochloride (547 g) in 92% yield as a white solid.

HPLC: sample preparation: 20 uL in 1 mL caustic for 15 min; AP=98% at 6.19 min (YMC Pack ODS-A, 3?m column 6.0×150 mm, 10–90% aqueous acetonitrile over 20 minutes containing 0.2% phosphoric acid, 2 mL/min, monitoring at 220 nm and 254 nm)

LC/MS: M+H=208

Chiral HPLC: RT=8.38 min, e.e. 100%, (Chiralcel OD-RH, 150×4.6 mm, eluent: acetonitrile: MeOH:20 mm Ammonium.Bicarbarbonate, pH 7.8 (15:15:70), flow rate 1 mL/min, 210 nM)

D. Preparation of 3-((R)-Hydroxymethyl)-morpholine-4-carboxylic acid tert-butyl ester

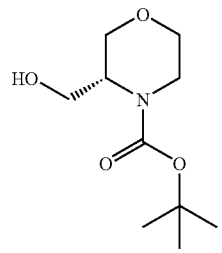

A mixture of [R-(4-benzyl-morpholin-3-yl)]-methanol hydrochloride (1 equiv.), aqueous $K_3PO_4$ (4.6 equiv.), and EtOAc was stirred until two clear phases were obtained. The EtOAc layer was separated, and the aqueous layer was extracted with fresh EtOAc. The combined EtOAc layers were charged into a flask containing 20 wt % $Pd(OH)_2$/C (50% water wet, 0.10 equiv based on input wt). Di-tert-butyl dicarbonate (1.2 moles) was added. The mixture was hydrogenated for 4h at 15 psi. After it was found complete by HPLC, the mixture was filtered through Celite and the solvent was exchanged to cyclohexane. The product was crystallized from cyclohexane (7–10 volumes) to afford the title compound as a white solid (yield 82%).

1H NMR (CDCl$_3$) δ 1.45 (s, 9H), 3.17 (m, 1H), 3.47 (dt, 1H, J=3.1, 11.4 Hz), 3.56 (dd, 1H, J=3.5, 11.9 Hz), 3.7–4.0 (m, 6H); $^{13}$C NMR (CDCl$_3$) δ 28.21, 40.01, 52.09, 59.59, 65.97, 66.49, 80.23, 155.30; MS: 218 (M+H)+; Anal. Calcd for C10H19NO4: C, 55.28; H, 8.81; N, 6.44. Found: C, 55.45; H, 8.87; N, 6.34; Pd <5 ppm; HPLC Ret Time: 5.28 min (YMC Pack ODS-A, 3 μm, 4.6×50 mm column, 10 min gradient, 2.5 mL/min); 100% ee [Chiral HPLC Ret Time: 13.6 min (Chiralcel OD-RH, 51 μm, 4.6×150 mm column, 20 min wasocratic method, 1 mL/min)].

E. Preparation of 5-Nitro-1-(3-fluorobenzyl)indazole (16)

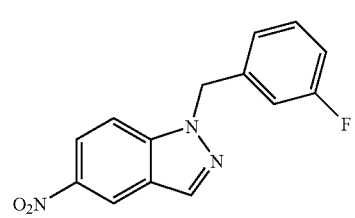

Compound 16

5-nitro indazole (1 equiv.), cesium carbonate (1.1 equiv.) and DMF (5 volumes) were charged to a vessel. The mixture was heated to 70–80° C. and 3-fluoro benzyl bromide was added over 75 mins. The reaction was assayed by HPLC for completion (<2 AP of nitro indazole vs combined isomers) and then cooled to 20° C. The salts were filtered and the cake was washed with DMF (2.7 volumes). The product was crystallized by charging water (1.35 to 1.45 volumes) between 15–21° C. The crystal slurry was held for 4 h, crystals were filtered and washed with 2:1 DMF:water mix (2.1 volumes), water (2 volumes) and finally 3:1 cold ACN:water mix (1.5 volumes). The wet cake was dried <45° C. to LOD <1% and the yield was about 49%

$^1$H NMR (CDCl$_3$) δ 5.64 (s, 2H), 6.87 (d, 1H, J=9.4 Hz), 6.95 (m, 2H), 7.30 (m, 1H), 7.42 (d, 1H, J=9.2 Hz), 8.23 (d of d, 1H, J=10 Hz and 2 Hz), 8.26 (s, 1H), 8.72 (d,1H, J=2 Hz); MS: 272 (M+H)+; HPLC Ret Time: 6.99 min (YMC ODS-A 3 um, 4.6×50 mm column, 10 min gradient, 2.5 mL/min).

F. Preparation of 1-(3-Fluoro-benzyl)-1H-indazol-5-ylamine (Compound C)

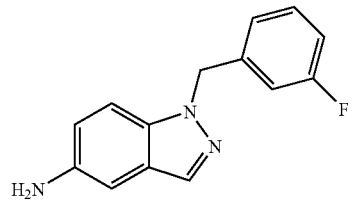

Compound C

Benzyl nitro indazole (1 equiv.) was charged to a hyrdogenator, THF (8 volumes) was added and hydrogenated at 15 psi between 30–40° C. The reaction mixture was held for ~1 h (s.m. <3% by HPLC) cooled to 25° C., the catalyst was filtered and the mixture was washed with THF (0.9 volumes). The mixture was transferred to another vessel, rinsed again with THF (0.4 volumes) distilled to the desired volume (5.5 volumes) atmospherically, and heptane was added (15 volumes) between 47–60° C. over 1 h. The slurry was cooled over 1.5 h to 18–23° C. The slurry was held for 1 h, filtered and washed with THF/heptane (1:4, 10.4 volumes) and dried in oven <45° C., (LOD <1%). yield was 84%. melting point=130° C. HPLC Ret Time: 9.09 min.

G. Preparation of 4-[1-(3-Fluoro-benzyl)-1H-indazol-5-ylamino]-5-methyl-pyrrolo[2,1-f][1,2,4]triazine-6-carboxylic acid ethyl ester (19)

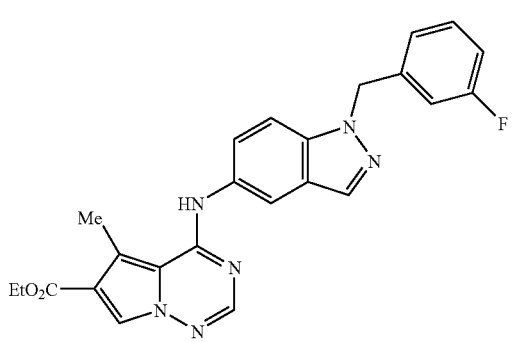

A 3-neck flask was charged with 5-methyl-4-oxo-3,4-dihydr-pyrrolo[2,1-f][1,2,4]triazine-6-carboxylic acid ethyl ester (1.00 equiv.) and dry toluene (15 volumes). POCl$_3$ (1.2 equiv.) was added in one portion, followed by slow addition of DIEA (1.1 equiv.) at a rate which maintained the temperature below 30° C. The resulting suspension was heated to 111° C. for 24 h becoming homogeneous at 80° C.

The reaction was monitored by HPLC after quenching with 2 M MeNH$_2$/THF (10 μL reaction mixture, 20 μL MeNH$_2$/THF in 200 μL acetonitrile). Upon completion, the reaction was cooled to −2° C. and was added to a solution of K$_2$HPO$_4$ (3.98 equiv) in H$_2$O (15.6 volumes) while maintaining the temperature below 10° C. The solution was stirred for 20 min at −22° C. The resulting light suspension was filtered through a pad of Celite and the layers were separated. The organic layer was washed with 23.5 wt % K$_2$HPO$_4$ in H$_2$O (2.94 volumes), followed by water (2.47 volumes). The solution was filtered and concentrated by heating over the temperature range of 22° C. to 58° C.; until HPLC ratio of toluene to 4-chloro-5-methylpyrrolo[2,1-f][1,2,4]triazine-6-carboxylic acid ethyl ester is 26–36%. The solution was cooled from 58° C. to 40–50° C. To the resulting suspension was added 1-(3-fluoro-benzyl)-1H-indazol-5-ylamine (0.988 equiv) and DIEA (1.1 equiv). The reaction was heated to 70–80° C. and held at this temperature until it was complete by HPLC. It was then cooled to 55° C. and isopropyl alcohol (15.5 volumes) was added. The mixture was cooled from 55° C. to 22° C. over a period of 1.8–2.2 hr. and filtered. The filter cake was washed with cold isopropyl alcohol (2×5.5 volumes) and dried under vacuum <50° C. to afford the product as a cream colored crystalline solid in 84% yield.

$^1$H NMR (500 MHz, CDCl$_3$) δ 1.39 (t, 3H, J=7.15 Hz), 2.93 (s, 3H), 4.35 (q, 2H, J=7.15 Hz), 5.59 (s, 2H), 6.86 (d, 1H, J=9.34H), 6.97 (m, 2H), 7.26 (ddd, 1H, J=6.04, 8.24, 14.29 Hz), 7.35 (d, 1H, J=8.80 Hz), 7.42 (br s, 1H), 7.49 (dd, 1H, J=1.65, 8.80 Hz), 7.91 (s, 1H), 8.00 (s, 1H), 8.07 (s, 1H), 8.09 (s, 1H); MS: 445 (M+H)$^+$; HPLC Ret Time: 3.847 min (YMC S5 ODS 4.6×50 mm column, 4 min gradient, 3 mL/min).

H. Preparation of 4-[1-(3-Fluoro-benzyl)-1H-indazol-5-ylamino]-5-methyl-pyrrolo[2,1-f][1,2,4]triazine-6-carboxylic acid (20)

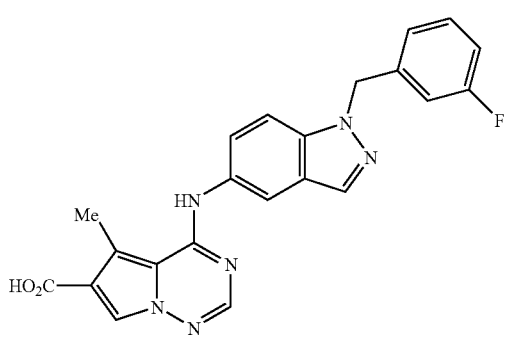

A flask equipped with mechanical stirrer was charged with 4-[1-(3-fluoro-benzyl)-1H-indazol-5-ylamino]-5-methyl-pyrrolo[2,1-f][1,2,4]triazine-6-carboxylic acid ethyl ester (19) (1 equiv), THF (4 volumes) and MeOH (2.5 volumes). The suspension was cooled to 5 C and 50% NaOH (5.3 equiv.) solution was slowly added maintaining the temperature below 15° C. The resulting solution was warmed to 60° C. for 4 h, and then cooled to 25° C. THF (7 volumes) was charged to the reaction and concentrated HCl (9.95 equiv.) was slowly added maintaining the temperature below 35° C. to pH 3. The resulting slurry was stirred at ambient temperature overnight, and then filtered. The filter cake was washed with H$_2$O (3×5 volumes) and dried on the filter for 1 h. The filter cake was washed with heptane (1×1 volume) and dried under vacuum at 50° C. to afford the product in 88% yield as an off-white solid.

$^1$H NMR (500 MHz, DMSO-d$_6$) δ 2.86 (s, 3H), 5.71 (s, 2H), 7.04 (m, 2H), 7.10 (dd, 1H, J=1.65, 8.80 Hz), 7.17 (d, 1H, J=7.70 Hz), 7.25 (t, 1H, J=7.70 Hz), 7.37 (dd, (1H, J=7.70, 13.74 Hz), 7.57 (dd, 1H, J=1.65, 8.80 Hz), 7.73 (d, 1H, J=8.80 Hz), 7.87 (s, 1H), 8.05 (d, 1H, J=8.35 Hz), 8.16 (s, 1H), 8.83 (s, 1H), 12.47 (s, 1H); MS: 417 (M+H)$^+$; HPLC Ret Time: 3.350 min (YMC S5 ODS 4.6×50 mm column, 4 min gradient, 3 mL/min).

27

I. Preparation of 3-[[[[[5-ethyl-4-[[(1-(3-fluorophenyl)methyl)-1H-indazol-5-yl]amino]pyrrolo[2,1-f][1,2,4]triazin-6-yl]amino]carbonyl]oxy]methyl]-4-morpholinecarboxylic acid, (3S)-1,1-dimethylethyl ester (21)

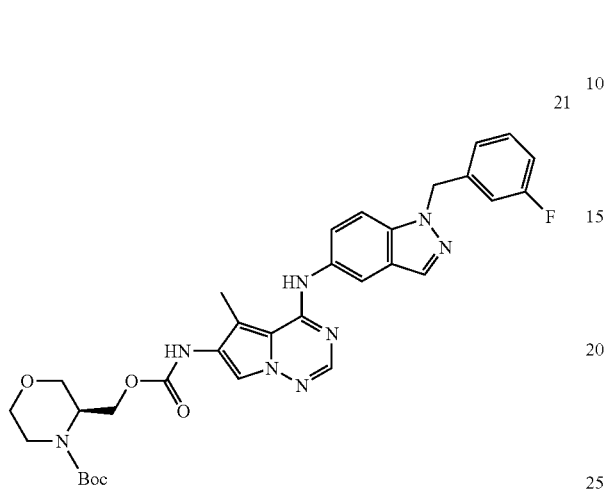

A flask was charged with 4-[1-(3-fluoro-benzyl)-1H-indazol-5-ylamino]-5-methyl-pyrrolo[2,1-f][1,2,4]triazine-6-carboxylic acid (20) (1 equiv.) and toluene (15 volumes). Residual water was removed by azeotropic distillation and the supernatant was analyzed for water content (KF: <200 ppm water). The flask was then charged with 3-hydroxymethyl-morpholine-4-carboxylic acid tert-butyl ester (1.05 equiv.) at about 77° C. Triethyl amine (1.2 equiv) and diphenylphosphoryl azide (1.2 equiv) were added between 77–85° C. The reaction was heated at ~87° C. until it was found complete by HPLC. The reaction was cooled to 25° C. diluted with THF (15 volumes) and washed with 10% $K_2CO_3$ (10 volumes), saturated NaCl (10 volumes) and water (10 volumes) respectively. The rich organic was polish filtered and distilled at atmospheric pressure until the pot temperature was >100° C. The final volume was adjusted to 15 volumes by adding toluene (if necessary). The mixture was cooled to 80° C., water (1 equiv) was added and the product was crystallized. The slurry was cooled to 25° C. over 1 h and held for 17 h. The solid was collected by filtration and the filter cake was rinsed with toluene (2×2 volumes). The solid was air dried overnight and then dried under vacuum at 50° C. to give the product in 82% yield.

$^1$H NMR (DMSO) δ 1.38 (s, 9H), 2.53 (m, 3H), 3.35–4.34 (m, 10H), 5.71 (s, 2H), 7.03–7.37 (m, 4H), 7.57 (d of d, 1H, J=9 Hz and 1.7 Hz), 7.70 (d, 1H, J=9 Hz), 7.82 (s, 1H), 8.08 (d, 1H, J=1 Hz), 8.15 (s, 1H), 8.58 (s, 1H); MS: 631 (M+H)+; HPLC Ret Time: 5.01 min (YMC ODS-A 3 um, 4.6×50 mm column, 10 min gradient, 2.5 mL/min).

28

J. Preparation of [4-[[1-(3-fluorophenyl)methyl]-1H-indazol-5-ylamino]-5-methyl-pyrrolo[2,1-f][1,2,4]triazin-6-yl]-carbamic acid, (3S)-3-morpholinylmethyl ester (Ia)

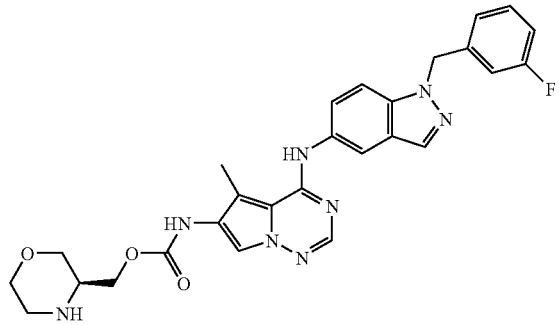

A flask was charged with 3-[[[[[5-ethyl-4-[[(1-(3-fluorophenyl)methyl)-1H-indazol-5-yl]amino]pyrrolo[2,1-f][1,2,4]triazin-6-yl]amino]carbonyl]oxy]methyl]-4-morpholinecarboxylic acid, (3S)-1,1-dimethylethyl ester (21)(1 equiv.), 7 volumes of water, 1 volume of methanol and concentrated HCl solution (5.0 equivalents). The slurry was heated to 70° C. and held at this temperature until found complete by HPLC. After completion, water (3 volumes) was charged into the hot reaction mixture which cooled the mixture to 45–55° C. The mixture was filtered and the filtrate was extracted with ethyl acetate (2×6 volumes). Ethyl acetate (10 volumes), methanol (2–3 volumes) and BHA (2.7 wt %) was charged into the isolated aqueous phase. Using 50% NaOH solution, the pH of the mixture was adjusted to pH 9–13. The phases were allowed to separate. The product rich organic layer was collected and water (10 volumes) was added into the mixture at 55–60° C. in 15–30 min. The mixture was held at 55–60° C. for 30 min after addition of water, then cooled to 19–25° C. over 1 h. The product was filtered and washed with ethyl acetate (2×3 volumes). The filter cake was reslurried with ethyl acetate (15 volumes) and BHA (2.7 wt %) was added. The resulting slurry was distilled at atmospheric pressure to remove moisture. The volume of the mixture was adjusted to 8–10 volumes while maintaining the batch temperature at 74–78° C. The mixture was cooled to 19–25° C. over an hour. The solid was collected by filtration and the filter cake was rinsed with ethyl acetate (2.2 volumes). The solid was dried under vacuum at 45° C. to afford a crystalline solid in 77% yield (HPLC AP 99.2).

$^1$H NMR (DMSO) δ 2.51 (m, 1H), 2.57 (s, 3H), 3.10–4.04 (m, 10H), 4.35 (m, 2H), 5.71 (s, 2H), 7.03–7.13 (m, 3H), 7.37 (m, 1H), 7.59 (m, 1H), 7.71 (m, 1H), 7.83 (s, 2H), 8.07 (s, 1H), 8.15 (s, 1H), 8.61 (s, 1H), 9.47 (s, 1H), 9.87 (s, 1H); MS: 531 (M+H)+; HPLC Ret Time: 4.55 min (YMC ODS-A 3 um, 4.6×50 mm column, 10 min gradient, 2.5 mL/min).

Additional compounds that can be prepared by the process of the invention include those shown in the following table wherein R, $R^1$ and $R^2$ are as shown.

TABLE

| R | R¹ | R² | Compound Name | [M + H] | HPLC Ret Time (min) |
|---|---|---|---|---|---|
| phenyl | ethyl | (3S)-morpholinylmethyl | [5-ethyl-4-[[(1-phenylmethyl)-1H-indazol-5-yl]amino]pyrrolo[2,1-f][1,2,4]triazin-6-yl]-carbamic acid, (3S)-3-morpholinylmethyl ester, monohydrochloride | 527 | 9.95 |
| phenyl | ethyl | (3R)-morpholinylmethyl | [5-ethyl-4-[[(1-phenylmethyl)-1H-indazol-5-yl]amino]pyrrolo[2,1-f][1,2,4]triazin-6-yl]-carbamic acid, (3R)-3-morpholinylmethyl ester | 527 | 10.06 |
| oxazol-2-yl | ethyl | (3S)-morpholinylmethyl | [5-ethyl-4-[[1-(2-oxazolylmetbyl)-1H-indazol-5-yl]amino]pyrrolo[2,1-f][1,2,4]triazin-6-yl]-carbamic acid, (3S)-3-morpholinylmethyl ester | 518 | 6.70 |
| thien-2-yl | ethyl | (3S)-morpholinylmethyl | [5-ethyl-4-[[1-(2-thienylmethyl)-1H-indazol-5-yl]amino]pyrrolo[2,1-f][1,2,4]triazin-6-yl]-carbamic acid, (3S)-3-morpholinylmethyl ester | 533 | 9.70 |
| 3-fluorophenyl | ethyl | (3S)-morpholinylmethyl | [5-ethyl-4-[[1-[(3-fluorophenyl)methyl]-1H-indazol-5-yl]amino]pyrrolo[2,1-f][1,2,4]triazin-6-yl]-carbamic acid, (3S)-3-morpholinylmethyl ester | 545 | 10.21 |
| thiazol-4-yl | ethyl | (3S)-morpholinylmethyl | [5-ethyl-4-[[1-(4-thiazolylmethyl)-1H-indazol-5-yl]amino]pyrrolo[2,1-f][1,2,4]triazin-6-yl]-carbamic acid, (3S)-3-morpholinylmethyl ester | 534 | 7.98 |
| thien-3-yl | ethyl | (3S)-morpholinylmethyl | [5-ethyl-4-[[1-(3-thienylmethyl)-1H-indazol-5-yl]amino]pyrrolo[2,1-[1,2,4]triazin-6-yl]-carbamic acid,(3S)-3-morpholinylmethyl ester | 533 | 9.68 |

TABLE-continued

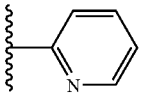

| R | R¹ | R² | Compound Name | [M + H] | HPLC Ret Time (min) |
|---|---|---|---|---|---|
| 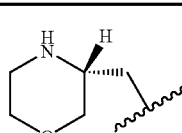 | ethyl | 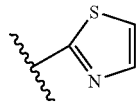 | [5-ethyl-4-[[1-(2-pyridinylmethyl)-1H-indazol-5-yl]amino]pyrrolo[2,1-f][1,2,4]triazin-6-yl]-carbamic acid, (3S)-3-morpholinylmethyl ester | 528 | 7.14 |
| 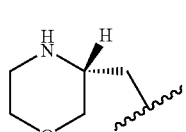 | ethyl | 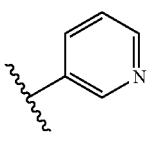 | [5-ethyl-4-[[1-(2-thiazolylmethyl)-1H-indazol-5-yl]amino]pyrrolo[2,1-f][1,2,4]triazin-6-yl]-carbamic acid, (3S)-3-morpholinylmethyl ester | 534 | 8.21 |
| 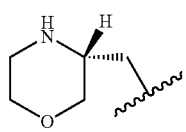 | ethyl | 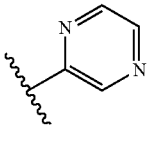 | [5-ethyl-4-[[1-(3-pyridinylmethyl)-1H-indazol-5-yl]amino]pyrrolo[2,1-f][1,2,4]triazin-6-yl]-carbamic acid, (3S)-3-morpholinylmethyl ester | 528 | 6.74 |
| 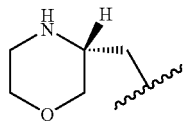 | ethyl | 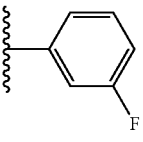 | [5-ethyl-4-[[1-(pyrazinylmethyl)-1H-indazol-5-yl]amino]pyrrolo[2,1-f][1,2,4]triazin-6-yl]-carbamic acid, (3S)-3-morpholinylmethyl ester | 529 | 7.46 |
| 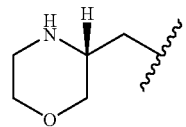 | methyl | 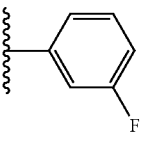 | [4-[[1-(3-fluorophenyl)methyl]-1H-methyl-pyrrolo[2,1-f][1,2,4]triazin-6-yl]-carbamic acid, (3S)-3-morpholinylmethyl ester | 531 | 2.48[2] |
| 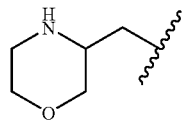 | methyl | 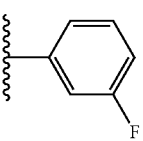 | [4-[[1-(3-fluorophenyl)methyl]-1H-indazol-5-ylamino]-5-methyl-pyrrolo[2,1-f][1,2,4]triazin-6-yl]-carbamic acid, 3-morpholinylmethyl ester | 531 | 1.97[2] |
| 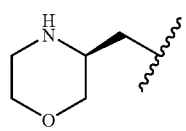 | methyl |  | [4-[[1-(3-fluorophenyl)methyl]-1H-indazol-5-ylamino]-5-methyl-pyrrolo[2,1-f][1,2,4]triazin-6-yl]-carbamic acid, (3R)-3-morpholinylmethyl ester | 531 | 1.97[2] |

What is claimed is:

1. A process for preparing compound (I) of the formula

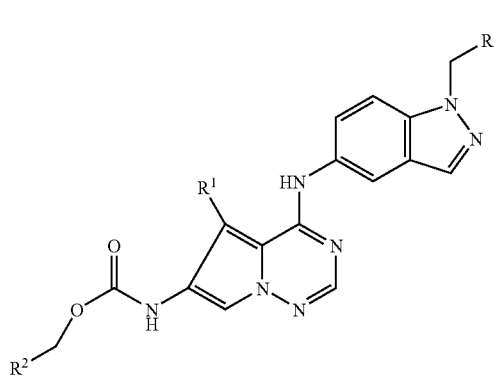

wherein
R is aryl, optionally substituted with alkyl or halogen or heterocyclyl;
$R^1$ is alkyl;
$R^2$ is heterocyclyl, optionally substituted with a BOC protecting group;
or a pharmaceutically acceptable salt or stereoisomer thereof,
which comprises the steps of
reacting Compound II of the formula or a tautomer thereof

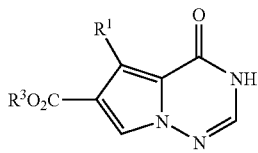

with an activating agent to afford Compound III of the formula,
where
X is a leaving group,
$R^1$ is as defined above, and
$R^3$ is lower alkyl

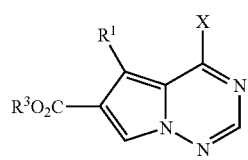

which is subsequently coupled with Compound IV of the formula

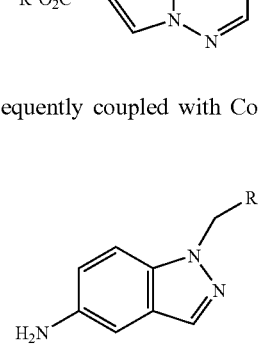

where R is as defined above, to afford Compound V of the formula

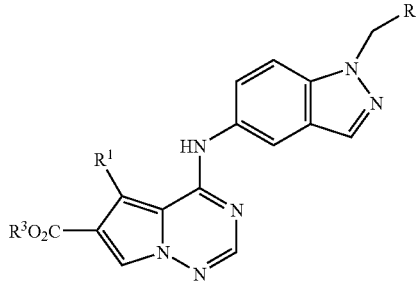

which is hydrolyzed to afford Compound VI of the formula

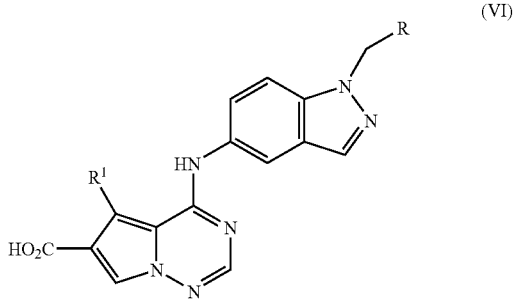

which subsequently undergoes a Curtius rearrangement in the presence of a compound of the formula —$R^2CH_2OH$ to afford Compound I.

2. The process as defined in claim 1 wherein —$R^2CH_2OH$ is Compound A of the formula

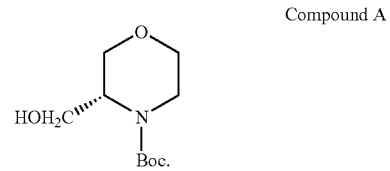

3. The process as defined in claim 1 wherein Compound I undergoes removal of an optional protecting group.

4. The process as defined in claim 1 wherein the activating agent is phosphorus oxyhalide or a Vilsmeier reagent.

5. The process as defined in claim 1 wherein the leaving group is a chloro, bromo or iodo group or a phosphorus ester.

6. A process for preparing compound (Ia) of the formula

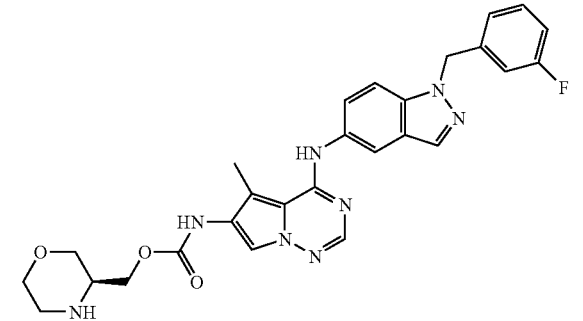

which comprises the steps of reacting Compound B of the formula or a tautomer thereof

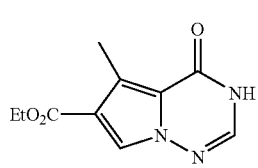

Compound B with a chlorinating agent to afford Compound 18 of the formula

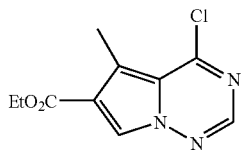

18 which is subsequently coupled to Compound C of the formula

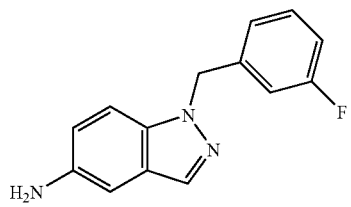

Compound C to afford Compound 19 of the formula

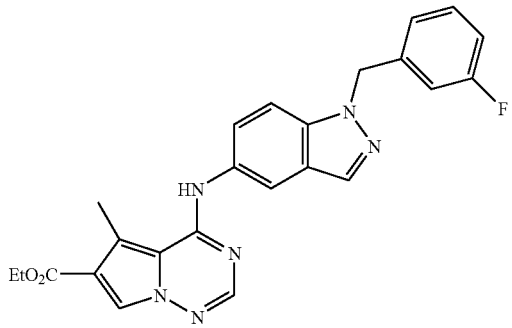

19 which is hydrolyzed to afford Compound 20 of the formula

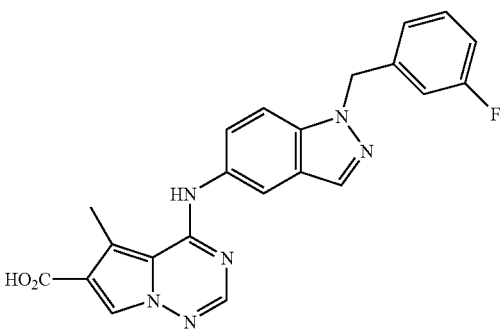

20 which undergoes Curtius rearrangement in the presence of Compound A of the formula

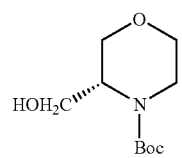

Compound A to afford Compound 21 of the formula

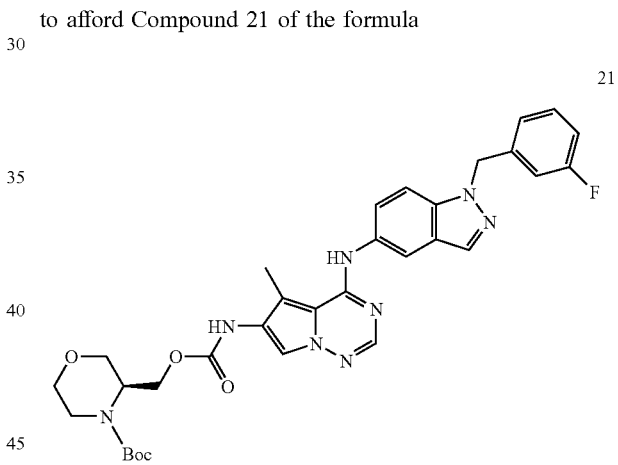

21 which is deprotected to afford Compound Ia.

* * * * *